United States Patent
Biagioni et al.

(10) Patent No.: US 9,889,132 B2
(45) Date of Patent: Feb. 13, 2018

(54) PHARMACEUTICAL COMPOSITIONS FOR THE TREATMENT OF PSORIASIS

(71) Applicant: Special Product's Line S.p.A., Pomezia (RM) (IT)

(72) Inventors: Daniele Biagioni, Gorfigliano di Minucciano (IT); Carlo De Angelis, Fontana Liri (IT); Lorenzo Scappaticci, Perugia (IT); Andrea Calcaterra, Rome (IT)

(73) Assignee: SPECIAL PRODUCT'S LINE S.P.A., Pomezia (IT)

( * ) Notice: Subject to any disclaimer, the term of this patent is extended or adjusted under 35 U.S.C. 154(b) by 0 days.

(21) Appl. No.: 15/323,462

(22) PCT Filed: Jul. 3, 2015

(86) PCT No.: PCT/EP2015/065231
§ 371 (c)(1),
(2) Date: Jan. 3, 2017

(87) PCT Pub. No.: WO2016/001419
PCT Pub. Date: Jan. 7, 2016

(65) Prior Publication Data
US 2017/0136015 A1    May 18, 2017

(30) Foreign Application Priority Data
Jul. 4, 2014  (IT) .............. MI2014A1224

(51) Int. Cl.
| | |
|---|---|
| *A61K 31/505* | (2006.01) |
| *A61K 9/00* | (2006.01) |
| *A61K 9/06* | (2006.01) |
| *A61K 31/341* | (2006.01) |
| *C07D 239/42* | (2006.01) |
| *C07D 407/04* | (2006.01) |
| *A61K 47/06* | (2006.01) |
| *A61K 47/44* | (2017.01) |
| *A61K 31/357* | (2006.01) |

(52) U.S. Cl.
CPC .......... *A61K 31/505* (2013.01); *A61K 9/0014* (2013.01); *A61K 9/06* (2013.01); *A61K 31/341* (2013.01); *A61K 31/357* (2013.01); *A61K 47/06* (2013.01); *A61K 47/44* (2013.01); *C07D 239/42* (2013.01); *C07D 407/04* (2013.01)

(58) Field of Classification Search
CPC ... C07D 407/04; C07D 239/52; C07D 239/46
See application file for complete search history.

(56) References Cited

U.S. PATENT DOCUMENTS

| | | | | |
|---|---|---|---|---|
| 2006/0183770 A1* | 8/2006 | Watanabe | ............ | C07D 261/08 514/310 |
| 2006/0205679 A1* | 9/2006 | Streeper | ............ | A61K 31/7048 514/26 |
| 2013/0085166 A1* | 4/2013 | Makra | ............ | A61K 31/215 514/352 |

FOREIGN PATENT DOCUMENTS

| | | |
|---|---|---|
| DE | 3414629 A1 | 11/1984 |
| EP | 0345362 A1 | 12/1989 |
| EP | 2108369 A1 | 10/2009 |
| FR | 2545356 A1 * | 11/1984 ........... C07D 239/42 |

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
M.A. Lowes et al., 32 Annual Reviews Immunology, 227-255 (2014).*
L. Hsu et al., Journal of Immunology Research (2014).*
English Language Machine Translation of FR 2545356 (1984).*
Pani A, et al., "The antimicotic drug 4,6-dimethyl-2-amino-3,4,5-trimethoxyphenyl-pyrimidine inhibits the nucleoside transport system of cells from various animal species", Experentia, vol. 50, Jan. 1, 1994, pp. 29-33.
Schivo M., et al., "Mitostatic action of 4,6-dimethyl-2-amino-3,4,5-trimethoxyphenyl-pyrimidine on mammalian cells", Experientia, vol. 32, No. 7, Jul. 15, 1976, pp. 911-913.
Search Report and Written Opinion of PCT/EP2015/065231 dated Aug. 31, 2015.

* cited by examiner

*Primary Examiner* — Alexander R Pagano
(74) *Attorney, Agent, or Firm* — Silvia Salvadori, P.C.; Silvia Salvadori

(57) ABSTRACT

Pharmaceutical compositions for topical administration for the treatment of psoriasis are described, containing as active ingredient therapeutically effective quantities of 4,6-dimethyl-N-(3,4,5-trimethoxyphenyl)pyrimidin-2-amine (I) and 2,4-O-(2-furanylmethylene)-1,3,5,6-tetra-O-methyl-D-glucitol combined with suitable excipients and/or diluents.

7 Claims, No Drawings

PHARMACEUTICAL COMPOSITIONS FOR THE TREATMENT OF PSORIASIS

This application is a U.S. national stage of PCT/EP2015/065231 filed on 3 Jul. 2015, which claims priority to and the benefit of Italian Application No. MI2014A001224 filed on 4 Jul. 214, the contents of which are incorporated herein by reference in their entireties.

FIELD OF INVENTION

The present invention relates to pharmaceutical compositions for topical administration in the treatment of psoriasis, containing as active ingredient therapeutically effective quantities of 4,6-dimethyl-N-(3,4,5-trimethoxy-phenyl)pyrimidin-2-amine (I) and 2,4-O-(2-furanylmethylene)-1,3,5,6-tetra-O-methyl-D-glucitol (II) combined with suitable excipients and/or diluents.

STATE OF THE ART

Psoriasis is a chronic inflammatory skin disorder which can affect any part of the body, but usually affects the scalp, elbows, knees, lumbar area of the back, genitals, palms of the hands and soles of the feet.

The aetiology of psoriasis is currently unknown, although genetic, immune and environmental factors, including infections of various kinds and metabolic dysfunctions, are certainly involved. Anyway this is a disorder which can arise at any age, and its incidence is greater in Caucasians than in persons with black ethnicity.

Various treatments have been proposed for this disorder. For example, A. Krebs and H. Shaltegger demonstrated the therapeutic efficacy of chrysarobin, a plant-based preparation extracted from *Andira Araroba*, mainly consisting of 1,8-dihydroxy-3-methyl-9-anthrone and dithranol (1,8-dihydroxy-9-anthrone), medicaments which have long been used to treat psoriasis, largely due to their cytostatic action (A. Krebs, H. Shaltegger, *Experientia*, 1965, 21, 128).

Many new treatments were later introduced. However, many of them are characterised by low efficacy and significant side effects. Moisturising creams based on salicylic acid are probably the most effective due to their keratolytic action. Other possible treatments are topical or systemic corticosteroids, treatments based on tar (which is highly irritant), and photochemotherapy with lamps at a wavelength of 312-313 nm, which can easily cause rashes and burns. Simultaneous administration of psoralens has led to PUVA; however, this treatment gives rise to various side effects such as nausea, headache, burning and itching.

Other recently discovered treatments include the use of chemotherapeutic or immunosuppressant agents such as cyclosporine A, methotrexate and some retinoids, such as etretinate. However, their use is limited to the most severe types of psoriasis, which do not respond to other topical treatments, because these medicaments give rise to various major side effects, especially their high liver toxicity.

The latest-generation treatments, however, use biopharmaceuticals, generally consisting of humanised or chimeric monoclonal antibodies, which interfere selectively, at various levels and with different action mechanisms, in the immunological processes that trigger and support psoriasis. These medicaments possess good activity and low organ toxicity, but are highly inadvisable for patients with a clinical history of tumours, and are ineffective in obese individuals. Some biopharmaceuticals have been withdrawn from the market due to their high toxicity and low efficacy, such as efalizumab, which caused progressive multifocal leukoencephalopathy.

Italian patent 1161221 discloses the therapeutic use of 4,6-dimethyl-N-(3,4,5-trimethoxyphenyl)pyrimidin-2-amine in the treatment of psoriasis. According to the studies conducted, the compound possesses considerable antimitotic action on mammal cells, and at the same time exhibits low toxicity, with an $LD_{50}$ per os in the mouse of 4110 mg/kg, and an $LD_{50}$ i.p., again in the mouse, of 780 mg/kg.

Although said active ingredient is more effective than the medicaments currently used, because it modulates the mitosis of cells affected by psoriasis and moderately reduces inflammation, it still does not provide an optimum solution to the problem of treating psoriasis.

DESCRIPTION OF THE INVENTION

It has recently been found that the combination of 4,6-dimethyl-N-(3,4,5-trimethoxyphenyl)pyrimidin-2-amine of formula I or a pharmaceutically acceptable salt thereof

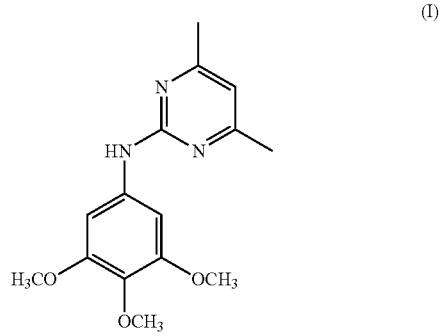 [SMILES: COc1cc(Nc2nc(C)cc(C)n2)cc(OC)c1OC]

(I)

with 2,4-O-(2-furanylmethylene)-1,3,5,6-tetra-O-methyl-D-glucitol of formula II

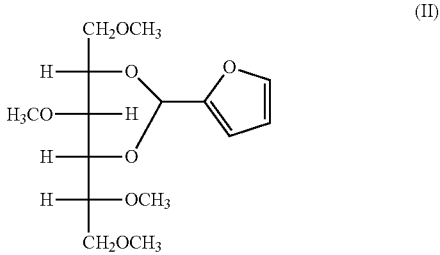

(II)

is more effective in the treatment of psoriasis.

The subject of the invention is therefore topical pharmaceutical compositions for the therapeutic treatment of psoriasis containing as active ingredient therapeutically effective quantities of 4,6-dimethyl-N-(3,4,5-trimethoxyphenyl) pyrimidin-2-amine (I) and 2,4-O-(2-furanylmethylene)-1,3,5,6-tetra-O-methyl-D-glucitol (II) combined with suitable excipients and/or diluents. The combination of said medicaments improves the efficacy of the known treatments giving a synergic effect, considerably enhance the period of relapse and does not give rise to side effects.

DETAILED DESCRIPTION OF THE INVENTION

The compositions according to the invention contain compound I in concentrations ranging between 1 and 10%, preferably between 2 and 5%, by weight of the total composition. Compound I can be present as such or in the form of a pharmaceutically acceptable salt. Examples of salts suitable for formulation include hydrochloride, salts with hydroxy benzoic acids such as salicylic acid (2-hydroxybenzoic acid) and gentisic acid (2,5-dihydroxybenzoic acid), and salts with sulphonic acids such as methanesulphonic acid, p-toluenesulphonic acid and butanedisulphonic acid. Salts with gentisic acid and with sulphonic acids are novel, and constitute a further subject of the invention. Moreover salification of I with hydroxy benzoic acids confers a keratolitic effect that can be modulated by the use of different acids.

The compound of formula II is present in the formulations according to the invention in concentrations ranging between 1 and 10%, preferably between 2 and 5%, by weight of the total composition.

The compounds of formula I and II will be formulated in compositions suitable for topical administration such as ointments, creams, suspensions, emulsions, fatty ointments, gels, powders, lotions and the like, using conventional techniques and excipients. Creams or ointments formulated with conventional excipients for cosmetic preparations, in particular vaseline, liquid paraffin and lanolin, are particularly indicated.

The compositions according to the invention can be administered once a day for periods of 8-10 days, not necessarily consecutive.

Example 1—Preparation of Pharmaceutical Composition Containing Compounds (I) and (II)

2 g of 4,6-dimethyl-N-(3,4,5-trimethoxyphenyl)pyrimidin-2-amine (I) and 2 g of 2,4-O-(2-furanylmethylene)-1,3,5,6-tetra-O-methyl-D-glucitol (II) are added to 100 g of vaseline.

The mixture is homogenised with a mechanical stirrer.

Example 2

Following a similar method to that described in the previous example, a pharmaceutical composition containing the following ingredients is prepared:

| | |
|---|---|
| compound (I) | 2.89 g |
| compound (II) | 3.16 g |
| liquid paraffin | 20 g |
| anhydrous lanolin | 30 g |
| vaseline | 44 g |

Example 3

The composition described in Example 2 was administered simultaneously to 10 patients suffering from psoriasis, on a specific psoriatic lesion, while a similar composition, but containing only compound (I) in salified form as active ingredient, was administered on another lesion of the same patients, in the same quantity as the composition described in example 2.

Both therapeutic compositions were administered to said patients once a day, every day.

On the whole, it was found in all patients that itching, redness and skin flaking disappeared more quickly in the part of the body treated with the composition described in example 2 than in the part treated with the composition containing compound (I) only, used as reference control. These effects (increased clinical efficacy and reduction of the onset of clinical response with respect to the single administration of each drug) can be attribute to the association of I and II which posses different activities, among which anti-inflammatory, keratolitic and antioxidant exhibited by the inhibitors of pro-inflammatory cytokines showing a synergic effect.

Moreover, after one month of treatment with the composition described in example 2, no relapses took place for at least 6 months.

The invention claimed is:

1. Topical pharmaceutical compositions containing as active ingredient 4,6-dimethyl-N-(3,4,5-trimethoxyphenyl)pyrimidin-2-amine (I) or a pharmaceutically acceptable salt thereof in concentrations ranging from 1 to 10% and
    2,4-O-(2-furanylmethylene)-1,3,5,6-tetra-O-methyl-D-glucitol (II) in concentrations ranging from 1 to 10%,
    in combination with suitable excipients and/or diluents.

2. Compositions according to claim 1 in the form of creams or ointments.

3. Compositions according to claim 2 wherein the excipients are vaseline, liquid paraffin or lanolin.

4. Compositions according to claim 1 in the form of suspensions or emulsions.

5. Compositions according to claim 1 wherein the compound of formula (I) is in the form of hydrochloride, salicylate or salts with hydroxy benzoic or sulphonic acids.

6. Method of treating psoriasis with the compositions according to claim 1, said method comprising:
    administering to a subject in need thereof the compositions according to claim 1, wherein said compositions comprise
    4,6-dimethyl-N-(3,4,5-trimethoxyphenyl)pyrimidin-2-amine (I) or a pharmaceutically acceptable salt thereof in concentrations ranging from 1 to 10% and
    2,4-O-(2-furanylmethylene)-1,3,5,6-tetra-O-methyl-D-glucitol (II) in concentrations ranging from 1 to 10%.

7. The topical pharmaceutical compositions according to claim 1, wherein a salt of 4,6-dimethyl-N-(3,4,5-trimethoxyphenyl)pyrimidin-2-amine is selected from salts with gentisic (2,5-dihydroxybenzoic) acid.

* * * * *